United States Patent [19]

Torrence et al.

[11] Patent Number: 4,515,781

[45] Date of Patent: May 7, 1985

[54] 2',5'-RIBOADENYLATE-MOR-PHOLINOADENYLATE NUCLEOTIDES

[75] Inventors: Paul F. Torrence, Gaithersberg, Md.; Margaret I. Johnston, Washington, D.C.; Jiro Imai, Kensington, Md.

[73] Assignee: The United States of America as represented by the Secretary of the Department of Health and Human Services, Washington, D.C.

[21] Appl. No.: 468,950

[22] Filed: Feb. 23, 1983

[51] Int. Cl.³ .................. A61K 31/70; C07H 15/12; C07H 17/00

[52] U.S. Cl. ........................ 514/46; 536/27; 536/28; 536/29; 514/48

[58] Field of Search .............. 536/27, 28, 29; 424/180

[56] References Cited

U.S. PATENT DOCUMENTS

| | | |
|---|---|---|
| 3,532,695 | 10/1970 | Dvonch et al. . |
| 3,542,776 | 11/1970 | Dvonch et al. . |
| 3,687,808 | 8/1972 | Merigan, Jr. et al. . |
| 3,759,890 | 9/1973 | Wilson . |
| 3,850,749 | 10/1974 | Kaufmann et al. . |
| 3,998,822 | 12/1976 | Yurugi et al. . |
| 4,000,137 | 12/1976 | Dvonch et al. . |
| 4,041,037 | 8/1977 | Dvonch et al. . |
| 4,210,746 | 7/1980 | Kerr et al. ............ 536/29 |
| 4,302,533 | 11/1981 | Revel et al. . |

OTHER PUBLICATIONS

J. C. Khym in Biochemistry, 2:344–350, (1963).
Brown et al., J. of Chem. Soc., 1965, pp. 5072–5074.

*Primary Examiner*—Johnnie R. Brown
*Assistant Examiner*—Elli Peselev
*Attorney, Agent, or Firm*—Holman & Stern

[57] ABSTRACT

Novel nucleotide compounds are afforded, having at least one 2',5'-riboadenylate unit and a terminal morpholinoadenylate unit. These compounds have potentiated biological activity in the 2,5-A system and increased resistance to degradation.

10 Claims, No Drawings

2',5'-RIBOADENYLATE-MORPHOLINOADENYLATE NUCLEOTIDES

BACKGROUND OF THE INVENTION

1. Field of the Invention

This invention relates to nucleotide compounds having at least one 2',5'-riboadenylate unit and a terminal morpholinoadenylate unit, which have potentiated biological activity.

2. Description of the Prior Art

Among the enzymes induced by interferon is 2-5A synthetase which, upon activation by certain double-stranded RNAs, converts ATP into a series of unique 2',5'-linked oligoriboadenylates bearing 5'-terminal triphosphate moieties.

2-5A refers to 2',5'-linked oligoriboadenylates of the general formula ppp5'A2'(p5'A)$\eta$. Different adenosine nucleotide residues of 2-5A are referred to as N-1, N-2, N-3, etc., where N-1 is the 5'-AMP unit comprising the 5-terminal residue bearing the triphosphate moiety, N-2 is the adjacent residue downstream 5'-AMP unit, etc. 2-5A synthetase refers to the enzyme that effects the conversion $\eta$ATP→ppp5'A2' (p5'A)n$_1$+$\eta$−1 pp, ($\eta \geq 2$) and has been variously referred to as 2-5A synthetase, 2-5A polymerase, 2',5'-nucleotidyl transferase, etc. The 2-5A-activated endoribonuclease has also been called RNase F or RNase L.

This generated 2-5A can activate a latent endoribonuclease, RNase L, which degrades RNA with a preference for cleavage after UpA, UpU, or UpG sequences. For this reason, 2-5A is a potent (IC$_{50}$∼10$^{-9}$ M) inhibitor of protein synthesis in cell-free extracts of eukaryotic cells.

The 2-5A system has been implicated in the mechanism of interferon's antiviral action. Thus, interferon induces the 2-5A synthetase in a potential host cell, and double-stranded RNA, generated by virus replication, triggers the enzyme to produce 2-5A which activates RNase L leading to the possible selective degradation of viral mRNA. Accordingly, the 2-5A system may be the primary pathway for the double-stranded RNA-induced inhibition of translation in extracts of interferon-treated mouse L-cells, and elevated levels of 2-5A, sufficient to effect protein synthesis inhibition, have been detected in mouse L-cells treated with interferon and subsequently infected with encephalomyocarditis virus.

In addition, a cell line, NIH-3T3 (clone 1), devoid of RNase L activity, failed to develop an interferon-induced antiviral state against encephalomyocarditis virus infection.

That the 2-5A system may not be limited to involvement in the mechanism of interferon's antiviral action, but may also be involved in cellular regulation and/or differentiation, has been suggested by the findings of high levels of 2-5A synthetase in diverse cell types such as reticulocytes, lymphocytes, lymphoblastoid cells, estrogen-stimulated and withdrawn chick oviduct cells, or cells from dog or mouse liver. Moreover, the 2-5A synthetase may be induced by treatment with agents other than interferon; for instance, dexamethasone in lymphoblastoid cells, dimethyl sulfoxide or sodium butyrate in Moloney sarcoma virus-transformed murine BALB/c cells (25), and dimethyl sulfoxide in cultures of Friend erythroleukemia cells. In this latter case, elevated synthetase levels were associated with erythroid differentiation and were apparently due to interferon production.

The capacity to employ 2-5A or its congeners directly in intact cells would be of great value since it would provide a means to study the biological role of the 2-5A derivatives as agonists or antagonists. In addition, the proposed role of the 2-5A system in the mechanism of interferon's antiviral action and in cell regulation or differentiation suggests its use as a novel approach to the chemotherapy of virus diseases or cancer. Such applications of 2-5A or its derivatives are limited by two established considerations. First, the 2-5A molecule has a relatively short half-life since it is rapidly degraded by a 2',5'-phosphodiesterase. Second, the 2-5A molecule itself, due to its ionic character, cannot penetrate the eukaryotic cell and is devoid of biological activity toward the untreated intact cell.

It was reported by J. C. Khym in *Biochemistry* 2:344-350 (1963) that he had modified a single nucleoside ribose ring to a morpholine, and a corrected molecular structure of this compound was published by Brown, et al., in *J. Chem. Soc.* 5072-5074 (1965). This is the most relevant prior art known to the inventors. However, the Khym compound is readily distinguishable from the compounds of this invention because it has (1) only a single ribose converted to a single morpholine, (2) only a methyl substitution at the N of the morpholine, (3) no phosphate moiety, and (4) no biological activity potentiation.

The inventors are also aware of the following U.S. patents, which are listed chronologically and not in relation to relevance.

U.S. Pat. Nos. 3,532,695 and 3,542,776 disclose the modification of periodate oxidized purine ribosides to morpholinoiso-nicotinamides.

U.S. Pat. No. 3,687,808 discloses the replacement of phosphates on a polynucleotide chain by thioanalogs, or linking such analogs to an existing phosphate.

U.S. Pat. No. 3,759,890 discloses imidazoyl derivatives of polysaccharides and polypeptides.

U.S. Pat. No. 3,850,749 discloses oligoribonucleotides including, typically, 2'(3')-O-isovaleryl ApApApA. There is no disclosure of a terminal morpholine, and all compounds have a 3',5'-internucleotide linkage.

U.S. Pat. No. 3,998,822 discloses morpholino-containing pyrido-pyridazines.

U.S. Pat. Nos. 4,000,137 and 4,041,037 disclose various synthetic nucleosides including inosine, adenosine and cytidine useful as antitumorals.

U.S. Pat. No. 4,210,746 discloses pppApApA, but there is no terminal morpholine.

U.S. Pat. No. 4,302,533 discloses (2'-5')pppApApA, but there is no terminal morpholine.

SUMMARY OF THE INVENTION

This invention affords a nucleotide compound having the molecular formula:

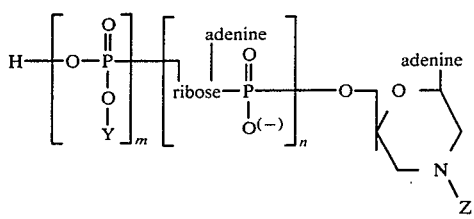

(I)

wherein m is 0, 1, 2, 3 or 4;

Y is always H except on the terminal phosphate where Y may be H, adenosine, or a $C_{1-20}$ primary or secondary alcohol;

n is an integer from 1 to 15; and

Z is H or a $C_{1-50}$ hydrocarbon or substituted hydrocarbon bonded to the N of the morpholino ring through one of its carbon atoms and which moiety preferably does not impede the compound's biological activity or stability.

The compounds of this invention are characterized by having biological activity potentiated beyond that of unmodified 2,5-A oligomers and by being substantially more resistant to degradation than 2,5-A oligomers. As a result, the compounds of this invention can act in vitro or in vivo (a) to circumvent interferon by mimicking and/or displacing it in the above-described system, (b) as an antagonist to block the action of interferon produced by the cells. Thus, the compounds of this invention can be used for fine tuning in antitumoral chemotherapy and to avoid interferon-induced auto-immune diseases such as systemic lupus erythematosus, and "auto-immune deficiency syndrome" as well as (c) as an investigative tool for the biological mechanisms of 2,5-A.

It is especially noted that the compounds of this invention have only a 2′,5′-internucleotide linkage, as critically distinguished from the more common 3′,5′ linkage.

DESCRIPTION OF THE PREFERRED EMBODIMENTS

Molecular formula I, described above, may also be written as

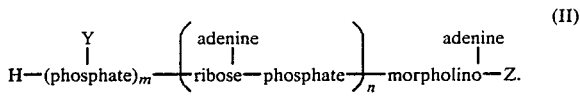

(II)

In either formula I or II, m may be 0, 1, 2, 3 or 4. The preferred forms of the compounds of this invention are the unphosphated (m=0), monophosphate (m=1) and the triphosphate (m=3). However, the diphosphate (m=2) and the tetraphosphate (m=4) forms of the compounds of this invention are also useful. It is believed that when m exceeds 3, the compounds will be increasingly subject to cleavage to the mono-and tri-forms.

In either formula I or II, Y is always H except on a terminal phosphate, where Y may be H, adenosine, or a $C_{1-20}$ primary or secondary alcohol. It is preferred that Y is H. Where Y is not H, the substituent moiety may act to modify the behaviour of the compound. For example, in using the invention compounds where Y is H, the most effective antiviral compounds are the triphosphates, but the monophosphates are more effective in "fine tuning" chemotherapy to prevent a bad toxic reaction to interferon or to treat autoimmune deficiency diseases. Generally, the diphosphates and tetraphosphates, (where Y is H), will behave like the triphosphates. An unphosphated compound will probably also behave like a triphosphate.

Where Y is a substituent moiety other than H: the tetraphosphate will behave similarly to the triphosphate when Y is H; the triphosphate will behave like either a monophosphate, or a triphosphate when Y is H; and the diphosphate and monophosphate will behave the same as the monophosphate when Y is H.

In either formula I or II, n may be an integer from 1 to 15. Because of possible variations in the method of synthesis, the value of n may be an average rather than an absolute number. Although ribose monomers (n=1) are useful in this invention, ribose low polymers (n=2 to 6) are preferred, and ribose oligomers (n=2, 3 or 4) are most preferred. The compounds may also be mixtures of these monomers and polymers.

In either formula I or II, Z may be H or a $C_{1-50}$ hydrocarbon or substituted hydrocarbon bonded to the N of the heterocyclic morpholino ring. The bonding should be through one of the C atoms of the substituent moiety and therefore any moiety not having a C atom free for such bonding is excluded from this invention. Also excluded are any substituent moieties which impede the desired biological activity or stability of the invention compounds.

Preferably, Z has the formula

wherein $R_1$ and $R_2$ (or Z itself) may be the same or different and may be hydrogen or any of the following moieties having $C_{1-50}$, preferably $C_{1-40}$, more preferably $C_{1-30}$, most preferably $C_{1-20}$:

(a) alcohols and their corresponding esters, ethers, and acids, saturated or unsaturated, branched or straight chain, preferably straight chain and unsaturated or sterols, including, but not limited to straight chain monohydric saturated alcohols such as 1-tetradecanol and 1-octacosanol, straight chain monohydric unsaturated alcohols such as cis-9-hexadecenol and cis-9-eicosenol, dihydric alcohols such as chimyl alcohol and selachyl alcohol, polyhydric alcohols such as glycerol and propylene glycol, substituted alcohols such as amino alcohols including amino-isopropanol and amino-cyclohexanel, (b) sterols (alicyclic alcohols) such as lanosterol, lupeol, alpha-amyrin, coprosterol, agnosterol, cholesterol, sitosterol, stigmasterol, brassicasterol, ergosterol, lumisterol, tachysterol, and 7-dihydrocholesterol, especially cholesterol and ergosterol, (c) alkanes such as ethane, isopentane, decane, nonadecane, and tetracentane, (d) alkenes such as propylene, butadiene, tetramethylethylene, and isoprene, (e) amino acids such as glycine, alanine, valine, leucine, isoleucine, phenylalamine, serine, threonine, methionine, cysteine, cystine, tyrosine, diiodotyrosine, thyroxine, tryptophan, aspartine, glutamine, lysine, arginine, and histidine,
(f) primary amines (although not secondary, tertiary or quaternary) such as butylamine, octylamine, and undecylamine,
(g) aromatic hydrocarbons such as benzene, xylene, naphthalene, coronene, and stilbene,
(h) cycloalkanes and cycloalkenes, such as cyclopropane, cyclopentene, spiropentane, and decalin,
(i) monoketones and acetone, such as acetone, diethyl ketone, and cyclohexanone,
(j) nitriles such as tripropionitrile, acrylonitrile, and malononitride,
(k) phenols which are monohydroxy such as phenol, cresols, naphthols, and alkylphenols,
(l) organic acids (in addition to those corresponding to the alcohols mentioned above) including
  n-saturated acids and their methylesters (except methanoic) such as pentanoic, tridecanoic, and tetracosanoic
  mono and poly-unsaturated fatty acids (except epoxy) such as 21-triacontenoic, 9,12-octadecadienoic, 9,12,15-octadecatrienoic, and 12-hydroxy-9-octadecenoic,
  branched chain fatty acids such as 3-methylbutanoic, 10-methylstearic, and 13-(2-cyclopentyl)-tridecanoic
  diacids more than $C_2$ such as malonic, succinic, adipic, azelaic, and phthalic From the extensive exemplary listings above, which are not intended to be limiting, it should be apparent that any substituent moiety at Z is useful for the purposes of this invention, provided always that it meets the critical limitations of
(1) always having a carbon free to bond to the nitrogen of the morpholino moiety,
(2) not being incompatible with the potentiated biological activity of the remaining portion of the invention compound,
(3) not being incompatible with the increased resistance to degradation of the remaining portion of the invention compound,
(4) not making the invention compound pharmaceutically incompatible when it is to be administered in vivo, and
(5) has a total number of carbon atoms of 1–50, preferably 1–40, more preferably 1–30, most preferably 1–20.

Of particular interest are compounds according to this invention which have already been synthesized, further details of which will be given below. Such compounds include those in which Z is a complex sugar, and in which Z is —CH—$R_1R_2$ and one of $R_1$ or $R_2$ is H while the other is pentyl, ε-aminopentyl, or

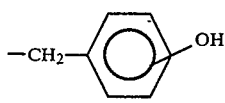

(para), or where both $R_1$ and $R_2$ are methyl.

Chemical modification of p5'A2'(p5'A2')n p5'A by a periodate oxidation/Schiff base formation/borohydride reduction cycle gave a series of 2-5A analogues in which the ribose of the 2'-terminal nucleotide was transformed to an N-substituted morpholine (azahexapyranose). 2',5'-Oligoriboadenylate 5'-monophosphates bearing this modification were 5–10 times more potent as antagonists of the action of 2-5A or poly(I)·poly(C) than was unmodified p5'A2'p5'A2'p5'A. Application of this modification to the tetramer triphosphate ppp5'A2'p5'A2'p5'A2'p5'A resulted in an analogue with 10 times the activity of ppp5'A2'p5'A2'p5'A(2-5A trimer triphosphate) as an inhibitor of protein synthesis or activator of the 2-5A-dependent endoribonuclease. This new 2-5A analogue, the most potent 2-5A derivative reported to date, inhibited translation in extracts of mouse L-cells programmed with encephalomyocarditis virus RNA at a concentration of $10^{-10}$M (concentration for half-maximal inhibition). All such N-substituted morpholine modified 2',5'-oligoriboadenylates were found to be extremely resistant to degradation by L-cell extracts under conditions where unmodified 2-5A or its derivatives were quickly destroyed. These data demonstrate the necessity for an intact terminal ribose ring for the action of the 2-5A phosphodiesterase. Thus, extensive chemical modification of 2' terminus of 2-5A may be possible without adversely affecting its biological activity while endowing it with other favorable properties such as resistance to degradation.

In the following discussion, the abbreviations used are: PEI, polyethyleneimine; EMCV, encephalomyocarditis virus; HPLC, high performance liquid chromatography; DMSO, dimethyl sulfoxide; dsRNA, double-stranded RNA; DMF, N,N-dimethyl formamide.

Oligonucleotides with 2',5'-phosphodiester linkages are considerably more resistant to emzymic degradation than their 3',5'-linked counterparts; nonetheless, at least one enzyme capable of degrading such 2',5'-linked oligomers, perhaps preferentially, has been documented in interferon-treated and untreated cell extracts. This enzyme degrades 2-5A (ppp5'A2'p5'A2'p5'A) from its 2' terminus, yielding 5'-AMP and 5'-ATP (from N-1 at the 5' terminus). In crude extracts, the 5' terminus (N-1) may not appear as ATP due to phosphatase action. It appears that the 2-5A degrading enzyme may be similar in substrate specificity to other described phosphodiesterases (e.g. snake venom phosphodiesterase from Crotalus atrox) in that modification of the terminal 2'(3')-ribose hydroxyl groups severely retards the rate of oligonucleotide chain scission. The phosphodiesterase activity responsible for degradation of 2-5A may require an intact terminal ribose with its 2'- and/or 3'-hydroxyl groups as recognition sites for enzyme action. This hypothesis is supported by the observations recorded herein on the metabolic stability of the 2' terminally modified oligoribonucleotides in which the entire 2'-terminal ribose ring has been replaced by a morpholine moiety in which no free hydroxyl group exists. In other studies, a putative cordycepin analogue of 2-5A, ppp5'(3'dA)2'p5'(3'A)2p5'(3'dA), has been reported to have enhanced stability in extracts of HeLa cells, and, under the same conditions used in this invention, the cordycepin analogue 5'-monophosphate, p5'(3'dA)2'p5'(3'dA)2'p5'(3'dA), was only 17% degraded after a 2 hour incubation. It has been found that the terminally 3'-O-methylated analogue, ppp5'A2'p5'A2'p5'A$_m$, had substantially increased lifetime in cell extracts when compared to 2-5A itself. Finally, it has been reported that 3' terminally phosphorylated derivatives of 2-5A were more stable to degradation by extracts of rabbit reticulocytes or Ehrlich ascites tumor cells.

The results of this invention also provide information on the oligonucleotide structural requirements for binding to and activation of the 2-5A dependent endoribonuclease (RNase L). Separation of binding and activation as discrete phenomena has been established previously. Since the 2′ terminally modified tetramer triphosphate 13 is a potent activator of RNase L, the extensive modification of the terminal ribose (N-4) implies that the corresponding N-4-terminal ribose site in ppp5′A2′p5′A2′p5′A2′p5′A must not be a significant contributor to binding and activation of the endonuclease. This is consistent with the observation, reported here and elsewhere, that 2-5A tetramer triphosphate, ppp5′A2′p5′A2′p5′A2′p5′A, and 2-5A trimer triphosphate, ppp5′A2′p5′A2′p5′A, are quite similar as activators of RNase L. Similarly, it has been reported that, in the reticulocyte system, ppp5′A2′p5′A2′p5′A2′p5′A and ppp5′A2′p5′A2′p5′A2′pA2′p5′Cp were equally effective as activators of RNase L, but, in the L-cell system, such as 3′ terminally monophosphorylated analogue was much ($\geq$30-fold) less active than the unmodified 2-5A. Since the 3′-O-methylated analogue, ppp5′A2′p5′A2′p5′A$_m$, was ascertained to be about 4 times more active than 2-5A trimer, as assayed by its ability to enhance RNA cleavage (42), the 3′-hydroxyl group of the terminal (N-3) nucleotide of 2-5A trimer triphosphate is probably not important for either endonuclease binding or endonuclease activation. The effect of substitution of hydrogen for the 3′-hydroxyl group of the terminal (N-3) riboside of 2-5A trimer is difficult to assess quantitatively since the biological activity of the trimer triphosphate in reticulocyte lysate is known to be anomalously low compared to tetramer triphosphate. The fact that the 2′ terminally modified trimer monophosphate 11 is more effective than p5′A2′p5′A2′p5′A as an antagonist of 2-5A action suggests that most, if not all, of the ribose moiety of the terminal (N-3) nucleotide of 2-5A trimer is not involved in binding to the endonuclease. In support of this conclusion, researchers have recently found that ppp5′A2′p5′A2′p5′(2′dA) is an effective activator of RNase L. All such conclusions must remain tentative, however, until direct nucleotide binding studies can be performed with endonuclease purified free of phosphodiesterase.

To summarize, conversion of the N-3- or N-4-terminal ribose ring of 2-5A to an N-substituted morpholine system (azahexapyranose) apparently did not impede binding to RNase L, but did thwart the action of the 2′,5′-phosphodiesterase which normally degrades 2-5A. This dramatically increased resistance to degradation correlated with the enhanced potency of the 2′-terminal ribose modified tetramer triphosphate 13 as an inhibitor of protein synthesis and activator of RNase L action. The increased metabolic stability may also be related to the increased activity of the 2′ terminally modified 2′,5′-oligoriboadenylate 5-′monophosphates 11 and 12 as antagonists of the action of 2-5A and poly(I) poly(C). So far as inhibition of translation and activation of enhanced RNA degradation are concerned, the modified tetramer triphosphate 13 is the most active 2-5A derivative reported to date. Such modified derivatives as 13 are readily available from 2-5A itself, and, perhaps most importantly, the nature of the modification permits further extensive alterations of the 2′ terminus of the 2-5A molecule.

EXAMPLES

Experimental Procedures

The preparation of cell extracts and the techniques and conditions of cell-free protein synthesis in extracts of interferon-treated or untreated mouse L cells have been described elsewhere.

Thin-layer chromatography was either on silica gel GF plates with system A (nBuOH/EtOH/H$_2$O/NH$_4$OH, 60:20:20:1) or system B (chloroform/methanol, 10:1), or on PEI cellulose plates with system C (0.1M NH$_4$HCO$_3$) or system D (0.25M NH$_4$HCO$_3$). HPLC was carried out with a Beckman instrument with model 110A pumps using an Ultrasphere ODS-C-18 column (4.6 mm×15 cm) with a flow rate of 1.0 mL/min. Elution was with an isocratic mix of 50 mM NH$_4$ H$_2$PO$_3$ (pH 7.2) (30%) and methanol-H$_2$O (1:1) (70%). Detection was at 260 nm.

Stability of 2′,5′-Oligoadenylates in Mouse L-Cell Extracts. Immunochemical Study Oligoadenylates at a final concentration of 400 nM were incubated under protein synthesis conditions (minus [$^3$H]-leu and EMCV RNA) at 30° C. for 0–6 hours. Samples were removed diluted with an equal volume of phosphate-buffered saline (PBS, 0.01M sodium phosphate, pH 7.4, 0.14M NaCl) with added 0.05% polyoxyethylene sorbitan monolaurate, (PSM) and then heated at 95° C. for 10–15 minutes. After cooling, the samples were centrifuged for 1 min. at room temperature in an Eppendorf microfuge. The supernatant samples were serially diluted (three-fold) in 0.05% PSM prior to analysis in a competitive enzyme-linked antibody assay.

Preparation of 2′-5′Oligoadenylate monophosphates (pA)$_n$ (n=2–4)

2′-5′-Oligoadenylate monophosphates (pA)$_n$ were prepared by lead ion catalyzed polymerization of adenosine 5′-phosphorimidazolide (ImpA)[4] or phosphorylation of properly protected A2′p5′A or A2′p5′A2′p5′A[5,6]. In the case of lead ion catalyzed polymerization, the polymerized reaction mixture was first treated with nuclease P$_1$ to remove undesired 3′,5′phosphate linkage isomers, and then separated on a DEAE Sephadex (HCO$_3$−) A-25 column eluted with triethylammonium bicarbonate (TEAB) buffer (pH 7.6) (linear gradient of 0.1M–0.75M). The purity of each oligomer was checked on PEI-cellulose tlc plates developed in 0.1M ammonium bicarbonate buffer (pH 7.5) and 1M lithium chloride.

Procedure for Derivatization (pA)$_n$ with Aliphatic Primary Amines as Illustrated by Preparation of Compound 12

To an ice cold solution of 2′-5′ (pA)$_4$ (415 OD$_{258}$, 10 umole) is H$_2$O (300 μl), 0.1M sodium metaperiodate (120 μl) was added. After the reaction mixture had been stirred on ice of 20 min., hexylamine (8 μl, 60 μmole) was added, and pH of the solution was immediately adjusted to 8.5 with 10% acetic acid. The reaction mixture was stirred on ice for another 20 min., and 0.5M sodium cyanoborohydride (100 μl) was added; the solution was again titrated with 10% acetic acid to pH 6.5 and allowed to stir on ice for 40 min. The reaction mixture was then applied to a DEAE Sephadex (HCO$_3$−) A-25 column (1.0×20 cm) which was eluted with a linear gradient (250 ml/250 ml) of 0.35M–0.40M TEAB (pH 7.6). Proper fractions were pooled, concentrated in vacuo, and co-evaporated with water several times in order to remove TEAB buffer. Hexylamine tailed (pA)$_4$ (12) was isolated as a sodium salt by dissolving the residue in methanol (300 μl) and pouring it into sodium iodide solution in dry acetone (50 mg/5 ml). The resulting precipitates were centrifuged, washed twice with dry acetone (each 3 ml) and dried over $P_2O_5$ under vacuum. The yield was 85% according to the OD reading at 258 nm (354 $OD_{258}$, 8.5 μmole). A similar procedure was employed to prepare all "tailed" oligonucleotide monophosphate.

Preparation of Triphosphate of 2'-Terminally Modified $(pA)_4$

Hexylamine tailed tetramer monophosphate compound 12, (354 $OD_{258}$, 8.5 μmole) was dissolved in dry DMSO (250 μl) and carbonyl diimidazole (9.5 mg, 58.6 μmole) was added to it. After being stirred at room temperature for 40 min., the whole reaction mixture was poured into sodium iodide solution in dry acetone (50 mg/6 ml). The resulting precipitate was centrifuged, washed with dry acetone (2×3 ml), and dried over $P_2O_5$ at room temperature in vacuo for 3 hours. 0.5M Tributyl ammonium pyrophosphate solution in DMF (200 μl) was added to this dried precipitate. The reaction mixture was allowed to stand at room temperature for 24 hours, followed by addition of cold water (1 ml). The diluted solution was then applied to a DEAE Sephadex ($HCO_3-$) A-25 column (1.0×20 cm) which was eluted with a linear gradient (250 ml/250 ml) of 0.30M TEAB to 0.60M TEAB (pH 7.6). After pooling and evaporation of proper fractions, the triphosphate 13 was isolated as a sodium salt in the same manner described above (133 $OD_{258}$), 3.2 μmole, yield 37.6%).31 P NMR ($D_2O$): −0.65, −0.77, −0.87, −5.63 (d, J=19 Hz), −10.70 (d, J=18 Hz). −20.89 (t, J=18 Hz). Compound 13 had a retention time of 7.19 min under the HPLC conditions described above and was ≧99% pure.

9-(3'-aza-4'-hexyl-1',2',3',4'-tetradeoxyhexopranos-1'-yl)-adenine [2-(9-adenyl)-6-hydroxymethyl-4-hexylmorpholine](7)

Adenosin (267 mg, 1 mmol) was dissolved in DMF (10 mL) and treated with 0.1M sodium metaperiodate solution (12 mL) in an ice bath. After 20 min. hexylamine was added to the reaction mixture, and the pH of the solution was adjusted to 8.6 with 0.5N HCl. The reaction mixture was stirred on ice for 10 min. and 0.5M sodium cyanoborhydride solution (10 mL) was added; the solution was again titrated with 0.5N HCl to pH 6.5 and allowed to stir on ice for 40 min. Water (20 mL) was added to the reaction mixture and the solution was extracted with ethyl acetate (4×40 mL). The combined organic layer was washed with sat. sodium bicarbonate solution and sat. sodium chloride solution, and then dried over anhydrous sodium sulfate. After the evaporation of solvent in vacuo the resulting solid residue was recrystallized from acetone to yield colorless crystals (302 mg, 0.905 mmol, yield 90.5%), mp 136°–138°, Anal. Calcd. for $C_{16}H_{26}O_2N_6$: C, 57–46; H, 7.84; N, 25.13. Found: C, 57.09; H, 7.85; n, 24.91.

Kinetics of 2-5 Synthesis in the Presence of Compound 11 or 12

A standard reaction mixture was composed of the following: 100 μls of a solution 180 mm KCl, 20 mM Mg(oAc)$_2$, 10 mM ATP, 40 mM Hepes (pH 7.5), 14 mM β-mercaptoethanol, 20% glycerol; 10 μl of either poly (I) poly (C) ($2.10^{-3}$ Mp) in 0.01M KCl, 0.01M Hepes (pH 7.5) or 0.01M KCl, 0.01M Hepes (pH 7.5) (−dsRNS control); 5 μLs of the potential inhibitor of 5 μLs of $H_2O$; 65 μLs of [$\alpha-^{32}P$]-ATP (30.8 Ci/mmole, 0.645 mCl/ml Amersham-Searle) in $H_2O$; 20 μL of micrococcal nuclease treated $S_{30}$ extract of interferon-treated (10 units/mL) mouse $L_k$cells. Incubation was at 30° for the designated times at which aliquots (35 μL) were removed and diluted 10× in cold $H_2O$. These diluted reaction mixtures were frozen at −90° until analysis.

Reaction mixture were analyzed by thin layer chromatography by spotting 2 μL of the diluted reaction mixture on a plastic PEI cullulose plate (E. Merck). The plate was developed first with solvent system D and then three times with solvent system C. After thorough drying in a well-ventilated hood, the plate was exposed to X-ray film (Kodak SB-5) for 18 hours with the aid of a Dupont Cronex intensifying screen. A template of the developed film was made with aid of tracing paper, and this was used to locate the corresponding radioactive spots on the tlc plate. The plate was cut according to the positions indicated by the template, and the resulting pieces were counted with 10 mls of fluor in a standard scintillation vial. The percentage of each radioactive component by the gross radioactivity associated with all the components visualized on tlc. The position of ATP, pp5'A2'p5'A,pppA2'p5'A2'p5'A, etc. were determined from authentic markers.

It is evident that neither "tailed" $(pA)_3$ nor "tailed" $(pA)_4$ had any significant effect on the rate of synthesis of 2-5A dimer triphosphate, trimer triphosphate or tetramer triphosphate. No 2-5A-related products were formed in the absence of poly (I) poly (C).

TABLE 1

"Tailing" of (2'→5')Oligoriboadenylate

| Oligoadenylates | | Step 1, periodate oxidation[a] | | | Step 2, hexylamine conjugation[a] | | | Step 3, reduction[a] | | | Main product[c,d] | | | By product[c] | | |
|---|---|---|---|---|---|---|---|---|---|---|---|---|---|---|---|---|
| compd | amt μmol | 0.1 M NaIO$_4$ μl | time min | pH | hexyl-amine μmol | time min | pH[b] | 0.5 M NaBH$_3$CN μl | time min | pH[b] | compd | amt μmol | % yield | compd | amt μmol | % yield |
| 1 | 1000 | 12 (ml) | 15 | 5.3 | 3000 | 10 | 8.6 | 10 (ml) | 20 | 7.0 | 7 | 8.05 | 80.5 | UI[e] | — | — |
| 2 | 100 | 1.2 (ml) | 20 | 5.3 | 600 | 10 | 8.6 | 1 (ml) | 40 | 6.8 | 8 | 87 | 87 | UI[e] | — | — |
| 3 | 10 | 120 | 20 | 5.2 | 40 | 10 | 8.6 | 100 | 40 | 6.5 | 9 | 8.6 | 86 | A2'p | 0.5 | 5 |
| 4 | 10 | 120 | 20 | 5.2 | 40 | 10 | 8.6 | 100 | 40 | 6.8 | 10 | 8.1 | 81 | p5'A2'p | 0.9 | 9 |
| 5 | 10 | 110 | 20 | 5.3 | 40 | 10 | 8.2 | 100 | 40 | 6.5 | 11 | 8.7 | 87 | p5'A2'p5'A2'p | 1.3 | 13 |
| 6 | 10 | 120 | 20 | 5.3 | 60 | 10 | 8.4 | 100 | 40 | 6.5 | 12 | 8.5 | 85 | p5'A2'p5'A2' | 1.0 | 10 |

TABLE 1-continued

| | | "Tailing" of (2'→5')Oligoriboadenylate | | | | | | | | | |
|---|---|---|---|---|---|---|---|---|---|---|---|
| Oligoadenylates | Step 1, periodate oxidation[a] | | Step 2, hexylamine conjugation[a] | | | Step 3, reduction[a] | | | Main product[c,d] | | By product[c] |
| compd | amt μmol | 0.1 M NaIO$_4$ μl | time min | pH | hexyl-amine μmol | time min | pH[b] | 0.5 M NaBH$_3$CN μl | time min | pH[b] | compd | amt μmol | % yield | compd | amt μmol | % yield |
| | | | | | | | | | | | | | | p5'A2'p | | |

[a]The reactions were performed at 0° C.–4° C.
[b]The pH of the reaction mixture was controlled with 5% acetic acid in each case except compd 1 which was titrated with 0.5N HCl.
[c]Each product was isolated as sodium salt after purification using DEAE Sephedex (HCO$_3$) A-25 column chromatography.
[d]Compound 7 was isolated as crystals mp 136°–138°, without using any column procedure.
[e]Unidentified.

For pilot studies on the derivatization of 2-5A and related oligonucleotides by the periodate oxidation/Schiff base formation/borohydride reduction sequence, adenosine and ATP were chosen as model substrates, and hexylamine were used as the amine Schiff base formation. Potential complicating side reactions such as β-elimination of the phosphate residue or decomposition of the resultant 3-azahexopyranose ring were not realized since excellent yields of 7 and 8 were obtained from adenosine or ATP when the pH of the medium was controlled carefully at 8.6 after the hexylamine conjugation and at 6.5 after the sodium cyanoborohydride reduction (Table 1).

Proof of the assigned structures, 7 and 8 (scheme I), was obtained from proton NMR (Table 2). In addition to two singlets assigned to adenine ring protons at δ 7.99 and 8.09 ppm, compound 7 revealed characteristic aliphatic chain proton signals at high magnetic field around δ 1.0 ppm. In addition, the side-chain methylene adjacent to nitrogen appeared as a triplet δ 2.40 ppm. The anomeric proton (H1') of the 3-azehexopyranose ring appeared at δ 5.76 ppm as a doublet of doublets ($J_1=3$ Hz, $J_2=10$ Hz) implying that the methylene protons were on a carbon adjacent to one bearing the anomeric proton. The 2'-methylene protons were found at δ 3.08 and 2/47 ppm as a doublet of doublets ($J_1=3$ Hz, $J_2=10$ Hz), and a triplet (J = 10 Hz), respectively. A highly split methine proton (H5') appeared at δ 3.85 ppm, and was coupled to H6' methylene protons at δ 3.55 ppm (doublet, J=5 Hz), and to H4' protons at δ 2.87 ppm (broad doublet, J=11 Hz) and 2.06 ppm (triplet, J=11 Hz). Considering the probable course of the reaction as determined by Brown and Read, supra, and the result of elemental analysis ($C_{16}H_{26}N_6O_2$), the above NMR data allowed the structure of the product to be assigned as 7[9-(3'-aza-4'-hexyl-1',2',3',4'-tetradeoxyhexopyranos-1'-yl)-adenine or 2-(9-adenyl)-4-hexyl-6-hydroxyl-methylmorpholine)].

TABLE 2

Proton NMR of "Tailed" Nucleotides[a]

| | Purine Ring | Ribose Ring(s) | | | |
|---|---|---|---|---|---|
| Compd | C-2' H & C-8H | C-1'H | C-2'H | C-3'H | C-4'H |
| 7 | 8.09 (1H, s) | | | | |
| | 7.99 (1H, s) | | | | |
| 8 | 8.10 (1H, s) | | | | |
| | 7.98 (1H, s) | | | | |
| 9 | 8.02 (1H, s) | 5.98 (1H, d) | 4.87 (1H, m) | 4.29 (1H, t) | 4.10 (1H, m) |
| | 7.98 (1H, s) | J = 5 | | J = 5 | |
| | 7.93 (1H, s) | | | | |
| | 7.80 (1H, s) | | | | |
| 10 | 8.22 (1H, s) | 6.05 (1H, d) | 4.86 (1H, m) | 4.37 (1H, t) | 4.20 (1H, m) |
| | 7.96 (1H, s) | J = 4 | | J = 5,8 | |
| | 7.93 (1H, s) | | | | |
| | 7.85 (1H, s) | | | | |
| 11 | 8.01 (1H, s) | 5.94 (1H, d) | 4.94 (1H, m) | 4.49 (1H, t) | 4.15 (1H, m) |
| | 7.85 (1H, s) | J = 4 | 4.58 (1H, m) | J = 5 | 4.08 (1H, m) |
| | 7.85 (1H, s) | 5.78 (1H, d) | | 4.20 (1H, t) | |
| | 7.81 (1H, s) | J = 3 | | J = 5 | |
| | 7.79 (1H, s) | | | | |
| | 7.74 (1H, s) | | | | |
| 12 | 7.95 (1H, s) | 5.88 (1H, d) | 4.83 (1H, m) | 4.41 (1H, t) | 4.08 (1H, m) |
| | 7.85 (1H, s) | J = 3 | 4.66 (1H, m) | J = 5 | 4.02 (1H, m) |
| | 7.84 (1H, s) | 5.73 (1H, d) | 4.55 (1H, m) | 4.31 (1H, t) | |
| | 7.77 (1H, s) | J = 4 | | J = 5 | |
| | 7.73 (1H, s) | 5.68 (1H, d) | | 4.21 (1H, t) | |
| | 7.73 (1H, s) | J = 3 | | J = 5 | |
| | 7.70 (1H, s) | | | | |
| | 7.64 (1H, s) | | | | |

| | Purine Ring | 3-aza-1,2,3,4-tetradeoxyhexopyranose Ring | | | |
|---|---|---|---|---|---|
| Compd | C-2' H & C-8H | C-1'H | C-2'H | C-4'H | C-5'H |
| 7 | 8.09 (1H, s) | 5.76 (1M, dd) | 3.08 (1H, dd) | 2.87 (1H, bd) | |
| | 7.99 (1H, s) | J = 3, 10 | J = 3, 10 | J = 11 | |
| | | | 2.47 (1H, t) | 2.06 (1M, t) | |
| | | | J = 10 | J = 11 | |
| 8 | 8.10 (1H, s) | 5.95 (1H, bd) | UD | UD | 4.23 (1H, m) |
| | 7.98 (1H, s) | J = 9 | | | |
| 9 | 8.02 (1H, s) | 5.66 (1H, bd) | 2.71 (1H, bd) | 3.92 (1M, m) | |

TABLE 2-continued

Proton NMR of "Tailed" Nucleotides[a]

| | | | | | |
|---|---|---|---|---|---|
| | 7.98 (1H, s) | J = 3, 10 | J = 9 | J = 10 | |
| | 7.93 (1H, s) | | 2.51 (1H, t) | 2.08 (1H, t) | |
| | 7.80 (1H, s) | | J = 9 | | J = 10 |
| 10 | 8.22 (1H, s) | 5.67 (1H, dd) | 3.22 (1H, dd) | 2.92 (1H, bd) | 3.95 (1H, m) |
| | 7.96 (1H, s) | J = 3, 9 | | J = 10 | |
| | 7.93 (1H, s) | | 2.71 (1H, t) | 2.18 (1M, t) | |
| | 7.85 (1H, s) | | J = 9 | J = 10 | |
| 11 | 8.01 (1H, s) | 5.54 (1H, dd) | 3.13 (1H, bd) | 2.89 (1H, bd) | UD |
| | 7.85 (1H, s) | J = 2, 8 | J = 9 | J = 9 | |
| | 7.85 (1H, s) | | 2.59 (1H, t) | | 2.17 (1H, t) |
| | 7.81 (1H, s) | | J = 9 | J = 9 | |
| | 7.79 (1H, s) | | | | |
| | 7.74 (1H, s) | | | | |
| 12 | 7.95 (1H, s) | 5.50 (1H, dd) | 3.08 (1H, bd) | 2.80 (1H, bd) | UD |
| | 7.85 (1H, s) | J = 2, 10 | J = 11 | J = 11 | |
| | 7.84 (1H, s) | | 2.54 (1H, t) | 2.06 (1H, t) | |
| | 7.77 (1H, s) | J = 11 | J = 11 | | |
| | 7.73 (1H, s) | | | | |
| | 7.73 (1H, s) | | | | |
| | 7.70 (1H, s) | | | | |
| | 7.64 (1H, s) | | | | |

| | Purine Ring | Hexyl Chain[b] | | |
|---|---|---|---|---|
| Compd | C-2' H & C-8H | C-6'H | H—$CH_2C_5H_{11}$ | $C_5H_{11}$—$CH_3$ |
| 7 | 8.09 (1H, s) | 3.55 (2H, d) | 2.40 (2H, m) | 0.87 (3H, t) |
| | 7.99 (1H, s) | J = 5 | J = 8 | J = 7 |
| 8 | 8.10 (1H, s) | 4.40 (1H, d) | UD | 0.66 (3H, t) |
| | 7.98 (1H, s) | J = 7 | | J = 7 |
| | | 4.02 (1H, d) | | |
| | | J = 7 | | |
| 9 | 8.02 (1H, s) | UD | 2.53 (2H, t) | 0.71 (3H, t) |
| | 7.98 (1H, s) | | J = 7 | J = 6 |
| | 7.93 (1H, s) | | | |
| | 7.80 (1H, s) | | | |
| 10 | 8.22 (1H, s) | 3.09 (2H, d) | 2.57 (2H, m) | 0.68 (3H, m) |
| | 7.96 (1H, s) | | | J = 7 |
| | 7.93 (1H, s) | | | |
| | 7.85 (1H, s) | | | |
| 11 | 8.01 (1H, s) | 3.69 (2H, d) | 2.51 (2H, m) | 0.67 (3H, m) |
| | 7.85 (1H, s) | | | J = 7 |
| | 7.85 (1H, s) | 5.78 (1H, d) | | 4.20 (1H, t) |
| | 7.81 (1H, s) | J = 3 | | J = 5 |
| | 7.79 (1H, s) | | | |
| | 7.74 (1H, s) | | | |
| 12 | 7.95 (1H, s) | 3.61 (2H, m) | 2.46 (2H, t) | 0.66 (3H, t) |
| | 7.85 (1H, s) | | J = 8 | J = 7 |
| | 7.84 (1H, s) | 5.73 (1H, d) | 4.55 (1H, m) | 4.31 (1H, t) |
| | 7.77 (1H, s) | J = 4 | | J = 5 |
| | 7.73 (1H, s) | 5.68 (1H, d) | | 4.21 (1H, t) |
| | 7.73 (1H, s) | J = 3 | | J = 5 |
| | 7.70 (1H, s) | | | |
| | 7.64 (1H, s) | | | |

[a] $^1$H NMR spectra were determined either at 200 MHz (7-11) or at 400 MHz (12) in $D_2O$ with acetone (2.05 ppm) as the internal standard except the case of 7, which was measured in $CD_3OD$ with tetramethylsilane as the standard. Only well-resolved characteristic signals are listed in the table. The data are presented in the following order: Chemical shift (δ, ppm). number of protons multiplicity and where appropriate coupling constant (J values are given in hertz). The multiplicity is represented as: singlet, s; doublet, d; triplet, t; doublet of doublets, dd; multiplet, m. Broad is abbreviated as b.

[b] The signals of the other methylene protons of the hexyl side chain were found as ~1.1-1.2 ppm and ~1.3-15 ppm.

A quite similar proton NMR spectral pattern was observed in the case of the product generated from ATP by the periodate oxidation/Schiff base formation/borohydride reduction sequence (Table 2). In this case however, the methyleneproton signals in H2', H4' and the hexyl side chain methylene adjacent to nitrogen overlapped each other and were difficult to distinguish, probably because all of the 3-azahexopyranose ring protons were shifted downfield by the paramagenetic effect due to the triphosphate moiety at the 6' position.. When compound 8 was digested by bacterial alkaline phosphatase at 37° overnight, the only product detected by thin layer chromatography was 7 (silica gel GF plate developed with system A or B or PEI cellulose developed with system C). Finally since compound 8 had nearly the same R, value as ATP on PEI cellulose tlc developed with 0.25M $NH_4HCO_3$, it is unlikely that the triphosphate moiety was affected during the reaction sequence. Thus, the structure of the product may be expressed as 8]9-(3'-aza-4-hexyl-1',2',3',4'-tetradeoxy-6'-triphosphorylhexopyranos-1'yl)-adenine] (Scheme 1).

No significant change in reaction conditions was necessary in 2'-terminals modification procedures for various 2',5'-linked oligoriboadenylates although some small amount (~10%) of oligoadenylate 2'(3'),5'-biphosphate was generated in each situation as a result of β-elimination of reaction intermediates. Reaction conditions and product yields in these procedures are presented in Table 1. With these procedures, the following 2',5'-linked oligoribonucleotides were modified with hexyl side chain: A2'p5'A(3), p5'A2'p5'A (4), p5'A2'p5'A2'p5'A (5) and p5'A2'p5'A2'p5'A2'p5'A (6)

(Scheme 1). These products (9, 10, 11, 12) were characterized chiefly by proton NMR of their sodium salts. As listed in Table 2, the anomeric protons of both the ribose ring(s) and 3-azahexopyranose rings as well as the H2' and H4' methylene protons of the 3'-azahexopyranose ring were observed as well-resolved signals in each case. Additional confirmation of the assigned structures was obtained by digestion of the oligoadenylates 9–12 with a mixture of snake venom phosphodiesterase and bacterial alkaline phosphatase at pH 8.8 and 37° overnight. Only adenosine and compound 7 were found to be generated in the correct ratio when analyzed on silica gel or PEI cellulose tlc in several different solvent systems (A-D). However, the oligomers 9–12 were unaffected by incubation with ribonuclease $T_2$ overnight at 37°. These findings strongly suggested that only the 2'-terminal ribose unit of the various 2'-5'-linked oligoriboadenylates were converted into the 3-aza-1',2',3',4'-tetradeoxyhexopyranose ring and that other portions of the molecule were not affected. The structures of the various products are, therefore, most reasonably expressed as 9–12 (Scheme 1). Compound 12, for instance may be named 5'-monophosphoryladenylyl-(2'→5')-adenylyl-(2'→5')adenylyl(2'→6')(3'-aza-4'-hexyl-1',2',3',4'-tetradeoxyhexopyranos-1'-yl)adenine.

The 5'-monophosphate 12 was converted to the corresponding 5'-triphosphate 13 (Scheme 2) by the conventional treatment of the imidazole of 12 with tri-n-butylammonium pyrophosphate. The desired triphosphate 13 was isolated as a sodium salt in a yield of 47% together with the corresponding 5'-diphosphate (~5%) and recovered starting material 12 (21%). The $^3P$ NMR spectrum of compound 13 revealed in addition to the three resonances of internucleotide phosphates, two doublets (J=19 Hz) at −5.62 ppm and −10.69 ppm and a triplet (J=19 Hz) at −20.74 ppm. These signals were assigned to the γ, α and β phosphorus atoms, respectively, of the 5'-triphosphate 13. HPLC analysis of this material on a reverse phase ODS column showed a purity of ≧99%.

Evaluation of the Biological Activity of the Modified (2'→5')Oligoriboadenylates.

Previous studies have shown that the 5'-monophosphorylated oligoribonucleotide, p5'A2'p5'A2'p5'A, can bind to the 2-5A-activated ribonuclease and prevent the protein synthesis inhibitory effects of 2-5A itself as well as poly(I)·poly(C). This observation provided a relatively simple approach to determine if a given nucleotide or oligoribonucleotide is capable of significant binding to the 2-5A-activated ribonuclease. For this reason, the (2'→5')oligoadenylates 5'-monophosphates, 11 and 12, were evaluated first for their ability to block the translational inhibitory effects of ppp5'A2'p5'A2'p5'A in extracts of mouse L cells programmed by encephalomyocarditis virus RNA. In the experiment, the 2-5A trimer, ppp5'A2'p5'A2'p5'A, was added in varying concentrations, with or without the tetranucleotide 5'-monophosphate inhibited translation with a concentration for half-maximal response of $\sim 2\times 10^{-9}$M in agreement with other values in the literature. However, when 12 was also present at a concentration of $8\times 10^{-5}$M, there was at least a 1000-fold increase in the concentration of 2-5A trimer triphosphate required to bring about a half-maximal inhibition of protein synthesis. The tetramer (12) itself had no significant effect on translation.

In order to gain some idea of how effective the 2'-terminally modified oligoribonucleotides were as antagonists of 2-5A action, they were compared to the unmodified trimer monophosphate p5'A2'p5'A2'p5'A in an experiment in which the concentration of 2-5A trimer triphosphate was held constant at 20 nM and the concentrations of p5'A2'p5'A2'p5'A, modified trimer monosphosphate (11), or modified tetramer monophosphate (12) were varied. Under these conditions, the concentration of (2'→5')oligoribonucleotide needed to prevent the action of 2-5A depended on the nature of the oligonucleotide. Comparison of the concentration necessary to effect a 50% decrease in the translational inhibition caused by 2-5A allowed the oligonucleotide monophosphates to be ranked in the following (decreasing) order of potency as antagonists of 2-5A action: modified tetramer monophosphate (12, $7\times 10^{-8}$M)>modified (11, $2\times 10^{-7}$)>p5'A2'p5'A2'p5'A($1.4\times 10^{-6}$M). The latter value for p5'A2'p5'A2'p5'A is in agreement with that reported previously.

To ascertain if the 2'-terminally modified (2'→5')oligonucleotides prevented the protein synthesis inhibitory action of 2-5A by the same mechanism as does p5'A2'p5'A2'p5'A (i.e., by preventing the activation of the 2-5A-dependent endoribonuclease), the 2-5A-enhanced degradation of [$^3$H]-encephalomyocarditis virus RNA was followed in extracts of mouse L cells in the presence or absence of the modified tetramer monophosphate (12). The 2-5A-activated degradation of encephalomyocarditis virus RNA was prevented by 12; furthermore, there was good agreement between the results since in both instances a concentration of $8\times 10^{-5}$M 12 caused approximately a 1000-fold increase in the concentration of ppp5'A2'p5'A2'p5'A needed to effect 50% of the maximum inhibition.

The oligomer p5'A2'p5'A2'p5'A can prevent most of the protein synthesis inhibition caused by poly(I)·poly(C) in extracts of interferon-treated mouse L cells. This observation implied that the inhibitory action of poly(I)·poly(C) is mediated chiefly by the 2-5A synthetase-endonuclease system. Since the modified oligonucleotides, 11 and 12, were found to be more effective antagonists of 2-5A action than p5'A2'p5'A2'p5'A itself, it was of interest to determine how effective such oligomers would be as antagonists of poly(I)·poly(C) action. In one experiment the concentration of poly(I)·poly(C) was kept constant at $2\times 10^{-6}$ Mp while the concentration of p5'A2'p5'A2'p5'A, modified trimer monophosphate (11) or modified tetramer monophosphate (12) were varied over a range of $2\times 10^{-4}$M to $10^{-8}$M. The behavior of p5'A2'p5'A2'p5'A was similar to that reported previously; that is the concentration required to reduce the maximal inhibition caused by poly(I)·poly(C) by 50% was approximately $10^{-5}$M. However, the 2'-terminally modified oligonucleotides were clearly superior in this regard since 11 and 12, at concentrations in the range of $10^{-6}$M, could cause a 50% reduction in the maximal poly(I)·poly(C) inhibition. In contrast to the experiment, wherein the tetramer 12 was somewhat more effective than the trimer 11 in preventing 2-5A action, in this case both 11 and 12 were of approximately equal potency in preventing the inhibitory action of poly(I)·poly(C). As observed previously with p5'A2'p5'A2'p5'A, the reversal of inhibition of poly(I)·poly(C) was not complete. Prevention of the action of poly(I)·poly(C) was not due to an inhibition of 2-5A synthesis since separate experiments established that neither 11 nor 12 affected the rate of formation of 2-5A under standard synthetase assay conditions.

Since the modified (2'→5')oligoriboadenylate 5'-monophosphates (11 and 12) were significantly superior to the unmodified p5'A2'p5'A2'p5'A as antagonists of the action of both 2-5A and poly(I)·poly(C), the corresponding terminally modified (2'→5')oligoriboadenylate tetramer 5'-triphosphate 13 was synthesized and evaluated as an inhibitor of protein synthesis in mouse L cell extracts programmed by encephalomycarditis virus RNA. In the experiment the tetramer triphosphate 13 was compared with 2-5A trimer triphosphate, ppp5'A2'p5'A2'p5'A, and 2-5A tetramer triphosphate, ppp5'A2'p5'A2'p5'A2'p5'A. For comparison purposes, the oligonucleotide concentration which achieved 50% of the maximum inhibition was determined for each compound: ppp5'A2'p5'A2'p5'A, $1 \times 10^{-9}$M, ppp5'A2'p5'A2'-p5'A2'p5'A, $5 \times 10^{-10}$M; modified tetramer triphosphate (13), $1 \times 10^{-10}$M. That 2-5A tetramer triphosphate is twice as active as 2-5A trimer triphosphate has not been reported before, but this result has been observed on a number different occasions with different L cell extracts and with different preparations of 2-5A tetramer triphosphate. It can be seen that terminally modified tetramer triphosphate (13) is 10-times more active than 2-5A trimer triphosphate and 5-times more active than 2-5A tetramer triphosphate as an inhibitor of cell-free protein synthesis. This result has been observed with two different preparations of 13 in several different L cell extracts.

The enhanced activity of the 2'-terminally modified tetramer triphosphate 13 also was observed when the degradation of [$^3$H]-encephalomycarditis virus RNA in cell extracts was examined. Modified tetramer triphosphate (13) enhanced degradation of labeled RNA with a concentration of $9 \times 10^{-11}$M necessary to elicit a half-maximal response compared to ppp5'A2'p5'A2'p5'A which required a concentration of $9 \times 10^{-10}$M to elicit a half-maximal response. In addition, there was good correlation between these values and the corresponding concentrations response for inhibition of protein synthesis.

To explore the possibility that the enhanced activity of the 2'-terminally modified (2'→5')oligoriboadenylates as antagonists of 2-5A action or activators of the 2-5A-dependent endoribonuclease resulted from increased resistance to degradation by various enzymatic activities in the cell extract, to the degradation of the modified and unmodified oligoribonucleotides was examined. First, the inactivation of 2-5A trimer triphosphate, ppp5'A2'p5'A2'p5'A, and the tetramer triphosphate 13 was followed by monitoring the decreased of their biological activities in a second mouse L cell-free system. Under conditions of protein synthesis in extracts of mouse L cells, the translation inhibitory capacity of modified tetramer triphosphate 13 was completely stable for at least 5 hours whereas the unmodified oligomer ppp5'A2'p5'A2'p5'A was rapidly destroyed with a half-life of about 15 minutes.

TABLE 3

| Reactivity of 2', 5'-Oligoadenylates with Antibody | | | |
|---|---|---|---|
| Unmodified | | "Tailed"-modified | |
| Compound | IC$_{50}$$^a$ | Compound | IC$_{50}$$^a$ |
| p5'A2'p5'A | ~300 | 10 | ~300 |
| p5'A2'p5'A2'p5'A | 8 | 11 | 5 |
| p5'A2'p5'A2'p5'A2'p5'A | 3 | 12 | 1 |
| ppp5'A2'p5'A2'p5'A | 18 | $^b$ | $^b$ |

TABLE 3-continued

| Reactivity of 2', 5'-Oligoadenylates with Antibody | | | |
|---|---|---|---|
| Unmodified | | "Tailed"-modified | |
| Compound | IC$_{50}$$^a$ | Compound | IC$_{50}$$^a$ |
| ppp5'A2'p5'A2'p5'A2'p5'A | 7 | 13 | 1 |

$^a$Concentration in nanomolar required to achieve a 50% inhibition of reactivity with anti-p5'A2'p5'A2'p5'A-serum in an enzyme-linked immunoassay.
$^b$This compound was not synthesized.

In a second series of experiments, the degradation of both the 5'-monophosphates and 5'-triphosphate of the terminally modified oligomers was compared to the degradation of the corresponding unmodified mono- and tri-phosphates. In this case, however, the course of reaction was followed using an immunoenzymometric assay for 2-5A and its derivatives. The antiserum employed in this study was inhibited 50% by both the unmodified and 2'-terminally modified 2',5'-oligoadenylates in the nanomolar range, the tetramer oligoadenylates being 2-5 times more reactive than the corresponding trimer species (Table 3, experimental). In contrast, the dimers were much less reactive, requiring concentrations of about 300 nM to achieve this same level of inhibition. Mononucleotides and adenosine were inhibitory only at millimolar concentrations.

The strong antibody reactivity with trimer and tetramer oligoadenylates and the much weaker reactivity with dimer and smaller species permitted the investigation of the stability of low concentrations of the trimer and tetramer 2',5'-oligoadenylates. When the unmodified 2',5'-oligoadenylates were incubated at a final concentration of $4 \times 10^{-7}$M oligomer under the modified protein synthesis conditions described in the experimental section, there was a rapid decrease in the presence of antibody reactivity material. The half life of p5'A2'p-5'A2'p5'A, p5'A2'p5'A2'p5'A2'p5'A or ppp5'A2'p-5'A2'p5'A2'p5'A was estimated to be 20-30 minutes. In contrast, the reactivity of antibody with the corresponding modified compounds (11, 12 and 13) did not decrease even after 6 hours of incubation. In fact, the reactivity of reaction mixtures containing 12 and 13 increased slightly with time. This increase might be attributed to the partial removal of 5'-terminal phosphates. The antibody reactivity is increased 3- and 8-fold when the 5'-terminal phosphate is removed from p5'A2'p5'A2'p5'A and p5'A2'p5'A2'p5'A2'p5'A, respectively, and is increased 10-fold when ppp5'A2'p-5'A2'p5'A2'p5'A is degraded to and A2'p5'A2'p5'A2'p-5'A. In view of the observation that the biological activity of 13 is not markedly decreased under the above conditions, the role of phosphatase activity must be minimal; however, the protein synthesis assay for 2-5A would not reliably detect a small (~50%) change in 2-5A concentration. Thus, a slow degradation of the 2'-terminally modified oligoadenylates may be masked, and the half-life estimation of 20-30 minutes for the corresponding unmodified polymers may be regarded as maximal. Assuming that 5'-terminal phosphatases are no more active on the 2'-terminally modified oligoadenylates than on unmodified polymers, these results confirm those observed by measuring biological activity; i.e., the 2'-terminally modified 2',5'-oligoadenylates (11, 12, 13) are markedly more stable in cell-free extracts than the unmodified 2',5'-oligoadenylates.

The numbered compounds referred to in this specification are identified as follows, reference being made to molecular formula I.

| compound | substituent | | | |
|---|---|---|---|---|
| | Y | m | n | Z |
| 10 | H | 1 | 1 | hexyl |
| 11 | H | 1 | 2 | hexyl |
| 12 | H | 1 | 3 | hexyl |
| 13 | H | 3 | 3 | hexyl |

We claim:

1. A nucleotide compound with a 2,5-internucleotide linkage having 1 to 15 riboseadenine unit and a terminal morpholine unit, having the formula

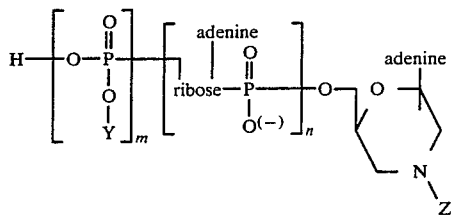

wherein:
Y is always H except on the terminal phosphate where Y may be H, adenosine, or a $C_{1-20}$ primary or secondary alcohol;
m is 0, 1, 2, 3 or 4;
n is an integer from 1 to 15; and
Z is H or a $C_{1-50}$ hydrocarbon or substituted hydrocarbon bonded through one of its C atoms to the N of the morpholino ring.

2. The compound of claim 1 wherein Z has 1–40 C atoms.
3. The compound of claim 1 wherein Z has 1–30 C atoms.
4. The compound of claim 1 wherein m is 0, 1 or 3.
5. The compound of claim 1 wherein Y is H.
6. The compound of claim 4 wherein Y is H.
7. The compound of claim 1 wherein n is from 2 to 6.
8. The compound of claim 7 wherein n is 2, 3 or 4.
9. A method of blocking the action of interferon produced by animal cells comprising using as an antagonist an effective amount of a nucleotide compound with a 2,5-internucleotide linkage having 1 to 15 ribose-adenine unit and a terminal morpholine unit, having the formula

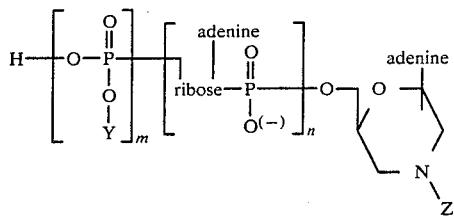

wherein:
Y is always H except on the terminal phosphate where Y may be H, adenosine, or a $C_{1-20}$ primary or secondary alcohol;
m is 0, 1, 2, 3 or 4;
n is an integer from 1 to 15; and
Z is H or a $C_{1-50}$ hydrocarbon or substituted hydrocarbon bonded through one of its C atoms to the N of the morpholino ring.

10. A method of treating interferon-induced autoimmune disease comprising administering to a host having said disease a pharmaceutically effective amount of a nucleotide compound with a 2,5-internucleotide linkage having 1–15 ribose-adenine unit and a terminal morpholine unit, having the formula

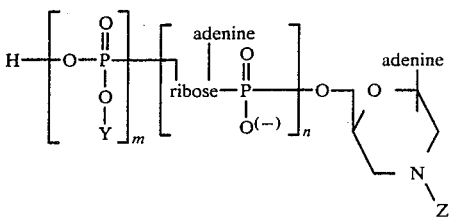

wherein:
Y is always H except on the terminal phosphate where Y may be H, adenosine, or a $C_{1-20}$ primary or secondary alcohol;
m is 0, 1, 2, 3 or 4;
n is an integer from 1 to 15; and
Z is H or a $C_{1-50}$ hydrocarbon or substituted hydrocarbon bonded through one of its C atoms to the N of the morpholino ring;
and a pharmaceutically acceptable carrier.

* * * * *